United States Patent
Foos et al.

(10) Patent No.: US 10,463,325 B2
(45) Date of Patent: Nov. 5, 2019

(54) MOBILE RADIOGRAPHIC APPARATUS/METHODS WITH TOMOSYNTHESIS CAPABILITY

(71) Applicant: CARESTREAM HEALTH, INC., Rochester, NY (US)

(72) Inventors: David H. Foos, Webster, NY (US); John Yorkston, Penfield, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 28 days.

(21) Appl. No.: 16/003,653

(22) Filed: Jun. 8, 2018

(65) Prior Publication Data

US 2018/0289345 A1    Oct. 11, 2018

Related U.S. Application Data

(60) Continuation of application No. 15/862,162, filed on Jan. 4, 2018, now Pat. No. 10,016,173, which is a
(Continued)

(51) Int. Cl.
*A61B 6/00* (2006.01)
*A61B 6/03* (2006.01)
*A61B 6/02* (2006.01)

(52) U.S. Cl.
CPC ............ *A61B 6/4405* (2013.01); *A61B 6/025* (2013.01); *A61B 6/03* (2013.01); *A61B 6/032* (2013.01);
(Continued)

(58) Field of Classification Search
CPC .................................................... A61B 6/4405
See application file for complete search history.

(56) References Cited

U.S. PATENT DOCUMENTS

| | | |
|---|---|---|
| 3,868,565 A | 2/1975 | Kuipers |
| 4,017,858 A | 4/1977 | Kuipers |

(Continued)

FOREIGN PATENT DOCUMENTS

| | | |
|---|---|---|
| CN | 101396275 | 4/2009 |
| CN | 102256547 A | 11/2011 |

(Continued)

OTHER PUBLICATIONS

International Search Report dated Jun. 3, 2013 for International Application No. PCT/US2013/027025, 2 pages.
(Continued)

*Primary Examiner* — Dani Fox

(57) ABSTRACT

A mobile radiography apparatus has a moveable (e.g., wheeled) transport frame and an adjustable column mounted at the frame. A boom apparatus supported by the adjustable column can support an x-ray source assembly. Radiation or X-ray source assembly methods and/or apparatus embodiments can provide mobile radiography carts a capability to direct x-ray radiation towards a subject from one or a plurality of different source positions, where the X-ray source assembly includes a first x-ray power source and a second plurality of distributed x-ray sources disposed in a prescribed spatial relationship.

20 Claims, 12 Drawing Sheets

Related U.S. Application Data division of application No. 14/375,944, filed as application No. PCT/US2013/027025 on Feb. 21, 2013, now abandoned.

(60) Provisional application No. 62/601,663, filed on Feb. 22, 2012.

(52) U.S. Cl.
CPC .......... *A61B 6/4007* (2013.01); *A61B 6/4028* (2013.01); *A61B 6/4283* (2013.01); *A61B 6/462* (2013.01); *A61B 6/464* (2013.01)

(56) References Cited

U.S. PATENT DOCUMENTS

| | | |
|---|---|---|
| 4,054,881 A | 10/1977 | Raab |
| 4,246,486 A | 1/1981 | Madsen |
| 4,298,874 A | 11/1981 | Kuipers |
| 4,314,251 A | 2/1982 | Raab |
| 4,752,948 A | 6/1988 | MacMahon |
| 4,836,671 A | 6/1989 | Bautista |
| 5,241,578 A | 8/1993 | MacMahon |
| 5,388,143 A | 2/1995 | MacMahon |
| 5,425,367 A | 6/1995 | Shapiro et al. |
| 5,539,798 A | 7/1996 | Asahina et al. |
| 5,550,889 A | 8/1996 | Gard et al. |
| 5,617,462 A | 4/1997 | Spratt |
| 5,646,525 A | 7/1997 | Gilboa |
| 5,751,783 A | 5/1998 | Granfors et al. |
| 5,949,811 A | 9/1999 | Baba et al. |
| 6,047,042 A | 4/2000 | Khutoryansky et al. |
| 6,154,522 A | 11/2000 | Cumings |
| 6,175,610 B1 | 1/2001 | Peter |
| 6,192,105 B1 | 2/2001 | Hunter et al. |
| 6,208,710 B1 | 3/2001 | Nagai |
| 6,327,336 B1 | 12/2001 | Gingold et al. |
| 6,404,851 B1 | 6/2002 | Possin et al. |
| 6,422,750 B1 | 7/2002 | Kwasnick et al. |
| 6,702,459 B2 | 3/2004 | Barnes et al. |
| 6,760,405 B2 | 7/2004 | Ruetten et al. |
| 6,895,268 B1 | 5/2005 | Rahn et al. |
| 6,942,385 B2 | 9/2005 | Fadler et al. |
| 6,944,266 B2 | 9/2005 | Yamazaki et al. |
| 6,950,492 B2 | 9/2005 | Besson |
| 7,010,091 B2 | 3/2006 | Hayashida et al. |
| 7,120,229 B2 | 10/2006 | Takasawa |
| 7,156,553 B2 | 1/2007 | Tanaka et al. |
| 7,345,274 B2 | 3/2008 | Nilsson |
| 7,368,724 B2 | 5/2008 | Morii et al. |
| 7,490,985 B2 | 2/2009 | Takekoshi et al. |
| 7,519,155 B2 | 4/2009 | Mollus et al. |
| 7,581,884 B1 | 9/2009 | Barnes et al. |
| 7,601,961 B2 | 10/2009 | Franklin et al. |
| 7,613,276 B2 | 11/2009 | Sendai |
| 7,632,016 B2 | 12/2009 | Huang et al. |
| 7,744,279 B2 | 6/2010 | Heath et al. |
| 7,780,350 B2 | 8/2010 | Tranchant et al. |
| 7,794,144 B2 | 9/2010 | Windt |
| 7,798,710 B1 | 9/2010 | Barnes et al. |
| 7,841,772 B2 | 11/2010 | Nishii et al. |
| 8,038,347 B2 | 10/2011 | Manak et al. |
| 8,821,015 B2 | 9/2014 | Stagnitto et al. |
| 8,821,017 B2 | 9/2014 | Lalena et al. |
| 8,824,634 B2 | 9/2014 | Lalena et al. |
| 8,827,554 B2 | 9/2014 | Lalena et al. |
| 8,867,705 B2 | 10/2014 | Lalena et al. |
| 8,873,712 B2 | 10/2014 | Wang et al. |
| 9,155,509 B2 | 10/2015 | Lalena et al. |
| 9,179,886 B2 | 11/2015 | Stagnitto et al. |
| 2002/0150215 A1 | 10/2002 | Barnes et al. |
| 2002/0188194 A1 | 12/2002 | Cosman |
| 2003/0165216 A1 | 9/2003 | Walker et al. |
| 2004/0101100 A1 | 5/2004 | Morii et al. |
| 2004/0105526 A1 | 6/2004 | Zhang et al. |
| 2005/0058244 A1 | 3/2005 | Tanaka et al. |
| 2005/0077085 A1 | 4/2005 | Zeller et al. |
| 2005/0169425 A1 | 8/2005 | Takasawa |
| 2006/0109958 A1 | 5/2006 | Ertel et al. |
| 2006/0269114 A1 | 11/2006 | Metz |
| 2007/0001905 A1 | 1/2007 | Eronen |
| 2007/0030957 A1 | 2/2007 | Pommi |
| 2007/0133747 A1 | 6/2007 | Manak et al. |
| 2007/0140419 A1 | 6/2007 | Souchay |
| 2007/0244388 A1 | 10/2007 | Sato et al. |
| 2007/0255087 A1 | 11/2007 | Minai |
| 2007/0297569 A1 | 12/2007 | Saunders |
| 2008/0002808 A1 | 1/2008 | De Godzinsky |
| 2008/0078940 A1 | 4/2008 | Castleberry et al. |
| 2008/0101536 A1 | 5/2008 | Sendai |
| 2008/0130837 A1 | 6/2008 | Heath et al. |
| 2008/0198968 A1 | 8/2008 | Takekoshi et al. |
| 2008/0204012 A1 | 8/2008 | Krueger et al. |
| 2008/0240343 A1 | 10/2008 | Jabri et al. |
| 2008/0240346 A1 | 10/2008 | Kashiwagi et al. |
| 2008/0240357 A1 | 10/2008 | Jabri et al. |
| 2009/0022264 A1* | 1/2009 | Zhou .............. A61B 6/025 378/5 |
| 2009/0032744 A1 | 2/2009 | Kito et al. |
| 2009/0060145 A1 | 3/2009 | Tranchant et al. |
| 2009/0086926 A1 | 4/2009 | Wang et al. |
| 2009/0136000 A1 | 5/2009 | Nishii et al. |
| 2009/0180590 A1 | 7/2009 | Borgmann et al. |
| 2009/0207973 A1 | 8/2009 | Yi |
| 2009/0257561 A1 | 10/2009 | Okuno et al. |
| 2009/0323893 A1 | 12/2009 | Hanke et al. |
| 2010/0002831 A1 | 1/2010 | Maack |
| 2010/0246759 A1 | 9/2010 | Ogura et al. |
| 2011/0002439 A1 | 1/2011 | Zhang |
| 2011/0075793 A1 | 3/2011 | Akahori et al. |
| 2011/0243303 A1 | 10/2011 | Vogtmeier |
| 2011/0249805 A1 | 10/2011 | Kralles et al. |
| 2011/0306864 A1* | 12/2011 | Zarate .............. A61B 6/4405 600/407 |
| 2011/0317816 A1 | 12/2011 | Bechard et al. |
| 2012/0039437 A1 | 2/2012 | Ren et al. |
| 2012/0189098 A1* | 7/2012 | Liu .............. A61B 6/4283 378/62 |
| 2012/0230473 A1 | 9/2012 | Stagnitto et al. |

FOREIGN PATENT DOCUMENTS

| | | |
|---|---|---|
| CN | 101946299 A | 1/2012 |
| JP | 2000-023955 | 1/2000 |
| JP | 2008-067933 | 3/2008 |
| JP | 2008-096998 | 4/2008 |
| JP | 2008-110098 | 5/2008 |
| JP | 2008-253758 | 10/2008 |
| JP | 2008-253762 | 10/2008 |
| JP | 2009-195500 | 9/2009 |
| JP | 2010-233962 | 10/2010 |
| JP | 2011-25012 | 2/2011 |
| JP | 2011-087917 | 5/2011 |
| JP | 2012-8567 | 1/2012 |
| WO | WO 2007/149402 | 12/2007 |
| WO | WO 2010/070560 | 6/2010 |
| WO | WO 2011/130207 | 10/2011 |

OTHER PUBLICATIONS

International Search Report, International application No. PCT/US2012/026221, dated Aug. 31, 2012, 2 pages.
Two-page brochure for EasyPos dental x-ray positioning system from website, Mar. 2010. hyphendev.fr file PubEasypos08v3.pdf.
International Search Report & Written Opinion, International application No. PCT/US2011/032035, dated Dec. 20, 2011, 2 pages.
International Search Report & Written Opinion, International application No. PCT/US2011/032020, dated Nov. 28, 2011, 2 pages.
European Search Report dated Oct. 19, 2015 for European Application No. 13751496.4, 2 pages.
Supplementary European Search Report completed Mar. 5, 2014 for European Patent Application No. 11 769 395.2, 2 pages.

(56) References Cited

OTHER PUBLICATIONS

Supplementary Partial European Search Report completed Apr. 29, 2014 for European Patent Application No. 11 769 406, 1 page.
European Search Report dated Jul. 15, 2014 for European Patent Application No. 12 754 539.0, 2 pages.

* cited by examiner

| Patient Name | Location | Exam | Exam Time |
|---|---|---|---|
| James Johnson | Rm 203 | Portable Chest | 4/11/2010 11:23:51 AM |
| Fred Smith | Rm 224 | Knee | 4/11/2010 11:24:12 AM |
| Fred Jones | Rm 245 | Portable Chest | 4/11/2010 11:23:44 AM |
| Scott Smith | Rm 252 | Portable Hip | 4/11/2010 11:24:05 AM |
| John Jones | Rm 483 | Portable Hip | 4/11/2010 11:22:48 AM |
| Bill Miller | Rm 508 | Portable Hip | 4/11/2010 11:23:37 AM |
| Bill Smith | Rm 572 | Knee | 4/11/2010 11:23:30 AM |
| Bill Miller | Rm 778 | Portable Chest | 4/11/2010 11:23:16 AM |
| Mike Jones | Rm 884 | Knee | 4/11/2010 11:23:23 AM |
| Robert Jones | Rm 944 | Portable Hip | 4/11/2010 11:23:02 AM |
| Fred Johnson | Rm 993 | Knee | 4/11/2010 11:23:58 AM |

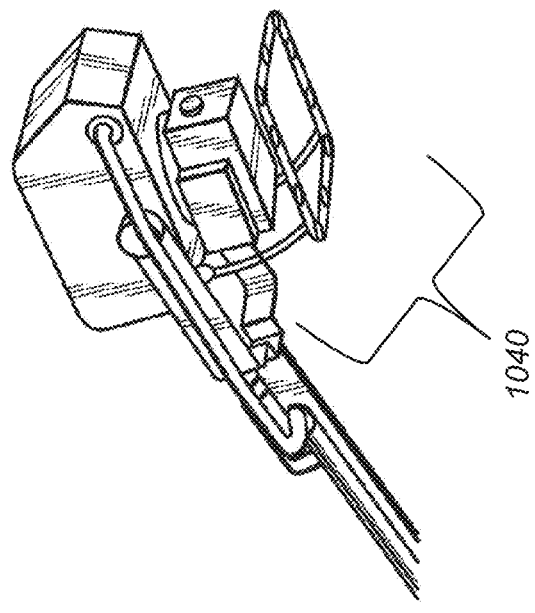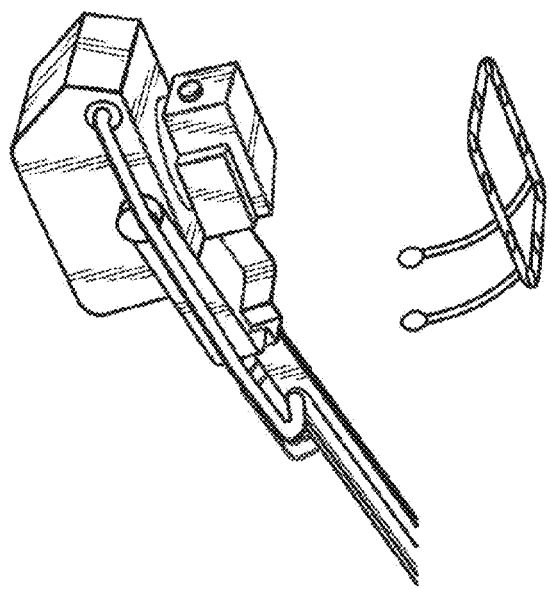
FIG. 10

MOBILE RADIOGRAPHIC APPARATUS/METHODS WITH TOMOSYNTHESIS CAPABILITY

CROSS REFERENCE TO RELATED APPLICATIONS

This application is a continuation application of U.S. patent application Ser. No. 15/862,162, filed Jan. 4, 2018, in the name of Foos, et al, entitled MOBILE RADIOGRAPHIC APPARATUS/METHODS WITH TOMOSYNTHESIS CAPABILITY, which is a divisional application of U.S. patent application Ser. No. 14/375,944, filed Jul. 31, 2014, in the name of Foos, et al. entitled MOBILE RADIOGRAPHIC APPARATUS/METHODS WITH TOMOSYNTHESIS CAPABILITY, which is itself a 371 National Stage Application of earlier filed PCT Application PCT/US2013/027025 filed Feb. 21, 2013 entitled MOBILE RADIOGRAPHIC APPARATUS/METHODS WITH TOMOSYNTHESIS CAPABILITY, in the name of Foos. et al., which claims the benefit of U.S. Provisional application U.S. Ser. No. 61/601,663, provisionally filed on Feb. 22, 2012, entitled PORTABLE TOMOSYNTHESIS SYSTEM USING DISTRIBUTED X-RAY SOURCE ARRAY, in the name of Foos, et al. which is hereby incorporated herein by reference in its entirety.

FIELD OF THE INVENTION

The invention relates generally to the field of medical imaging, and in particular to mobile radiographic imaging apparatus. More specifically, the invention relates to a mobile radiography apparatus having additional tomosynthesis capability.

BACKGROUND

Tomography (also referred to as x-ray computed tomography or computed tomography (CT)) is a well known medical digital imaging method created by computer processing. Digital image processing is used to generate a three-dimensional image of the inside of an object from a series/collection of two-dimensional x-ray images taken around a single axis of rotation. In CT, a source/detector makes a complete 360-degree rotation about the subject obtaining a complete volume of data from which images may be reconstructed. The volume of data produced by the CT system is manipulated to generate body structures. The images can be generated in the axial or transverse plane (e.g., perpendicular to the long axis of the body) or reformatted in various planes or a volumetric three-dimensional representation.

Tomosynthesis combines digital image capture and processing with source/detector motion used in tomography. While there are some similarities to CT, some view it as a separate technique. As noted above, in CT, the source/detector makes a complete 360-degree rotation about the subject obtaining a complete set of data from which images may be reconstructed. In digital tomosynthesis, a small rotation angle (e.g., 30 degrees) with a small number of discrete slices/exposures (e.g., 10) are used. This incomplete set of data is digitally processed to yield images similar to tomography with a limited depth of field. Since the image is digitally processed, a series of slices at different depths and with different thicknesses can be reconstructed from the same acquisition, thereby saving time and radiation exposure. Because the tomosynthesis data acquired is incomplete, tomosynthesis does not offer the narrow slice widths that CT offers.

SUMMARY OF THE INVENTION

An aspect of this application is to advance the art of mobile radiography.

Another aspect of this application to address in whole or in part, at least the foregoing and other deficiencies in the related art.

It is another aspect of this application to provide in whole or in part, at least the advantages described herein.

Another aspect of the application is to provide methods and/or apparatus by which mobile radiography carts can additionally include tomosynthesis capabilities.

Another aspect of the application is to provide methods and/or apparatus by which mobile radiography carts can be modified to operate in a first mode to obtain at least one general radiography projection image of an object using a first type central x-ray source, and to operate in a second mode to obtain a plurality of x-ray tomosynthesis projection images of an object using a plurality of second type distributed x-ray sources.

Another aspect of the application is to provide methods and/or apparatus by which mobile radiography carts can include an X-ray source assembly including a first central x-ray high power source and a second plurality of distributed x-ray lower power sources disposed in a prescribed spatial relationship.

Another aspect of the application is to provide methods and/or apparatus by which mobile radiography carts can include an X-ray source assembly including a plurality of distributed x-ray power sources where at least one central source of the distributed x-ray power sources has full (e.g., standard) X-ray power.

In accordance with one embodiment, the present invention can provide a mobile radiography apparatus that can include a moveable transport frame, an adjustable support structure coupled to the moveable transport frame, an x-ray source assembly mounted to the adjustable support structure configured to direct x-ray radiation towards a subject from one or a plurality of different source positions, where the x-ray source assembly includes a first x-ray power source and a second plurality of distributed x-ray sources disposed in a prescribed spatial relationship, control circuitry at the mobile x-ray radiography apparatus and coupled to the x-ray source assembly, the control circuitry configured to receive projection image data sets for reconstruction of tomosynthesis images.

In accordance with one embodiment, the present invention can provide a method for operating a portable x-ray radiography apparatus, the method can include one or more processors performing processes for operating in a first mode, where operating in the first mode includes obtaining at least one general radiography projection image of an object using a first type central x-ray source, and generating a reconstruction of the object using the at least one general radiography projection image, and operating in a second mode, where operating in the second mode includes obtaining a plurality of x-ray tomosynthesis projection images of an object using a plurality of second type distributed x-ray sources disposed in a prescribed spatial relationship, and generating a three-dimensional reconstruction of the object using the x-ray projection images.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of exemplary embodiments of the invention, as illustrated in the accompanying drawings.

The elements of the drawings are not necessarily to scale relative to each other.

FIGS. 5-8 are diagrams that illustrate exemplary functions implemented at an embodiment of a second display of a mobile x-ray imaging apparatus.

FIG. 10 is a diagram that shows exemplary mobile radiographic imaging systems including an x-ray source assembly embodiment that can include first and second radiographic x-ray sources according to the application.

DESCRIPTION OF EXEMPLARY EMBODIMENTS

Figure 1:
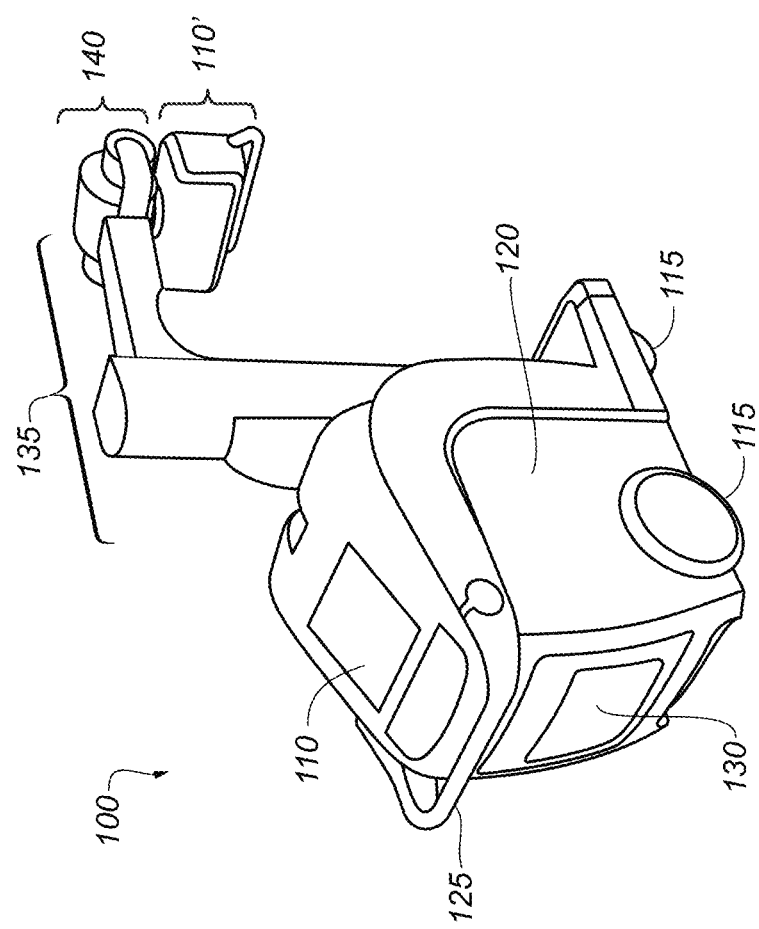
FIG. 1 is a diagram that shows a perspective view of a mobile radiography unit with a second display according to one embodiment of the application.

Applicants have recognized a need for a portable tomosynthesis systems and/or methods using distributed x-ray source arrays in mobile radiographic systems and/or methods for using the same.

Mobile radiographic systems are routinely used in hospitals. Compared to standard projection radiography, tomosynthesis provides improved depiction of fine details not visible in normal radiographs due to overlying structures. Such exemplary benefits of tomosynthesis provide the impetus to develop mobile tomosynthesis systems that can be utilized in the intensive care unit, emergency department, and operating rooms where moving patient is either impracticable or ill advised due to the risk of doing further damage to the patient.

The following is a description of exemplary embodiments of the invention, reference being made to the drawings in which the same reference numerals identify the same elements of structure in each of the several figures. Where they are used, the terms "first", "second", and so on, do not necessarily denote any ordinal or priority relation, but may be used for more clearly distinguishing one element or time interval from another.

FIG. 1 is a diagram that shows a perspective view of a mobile radiography unit that can use portable radiographic detectors or flat panel detectors according to embodiments of the application. The exemplary mobile x-ray or radiographic apparatus of FIG. 1 can be employed for digital radiography (DR) and/or tomosynthesis. As shown in FIG. 1, a mobile radiography apparatus 100 can include a moveable transport frame 120 that includes a first display 110 and an optional second display 110' to display relevant information such as obtained images and related data. As shown in FIG. 1, the second display 110' can be pivotable mounted at the x-ray source 140 to be viewable/touchable from a 360 degree area.

The displays 110, 110' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s).

For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) can provide source power, which can reduce or eliminate the need for operation near a power outlet. Further, the self-contained battery pack can provide for motorized transport.

For storage, the mobile radiographic apparatus 100 can include an area/holder for holding/storing one or more digital radiographic (DR) detectors or computed radiography cassettes. The area/holder can be storage area 130 (e.g., disposed on the frame 120) configured to removably retain at least one digital radiography (DR) detector. The storage area 130 can be configured to hold a plurality of detectors and can also be configured to hold one size or multiple sizes of DR detectors and/or batteries therefore.

Mounted to frame 120 is a support column 135 that supports an x-ray source 140, also called an x-ray tube, tube head, or generator that can be mounted to the support member 135. In the embodiment shown in FIG. 1, the support member (e.g., column 135) can include a second section that extends outward a fixed/variable distance from a first section where the second section is configured to ride vertically up and down the first section to the desired height for obtaining the image. In addition, the support column is rotatably attached to the moveable frame 120. In another embodiment, the tube head or x-ray source 140 can be rotatably coupled to the support column 135. In another exemplary embodiment, an articulated member of the support column that bends at a joint mechanism can allow movement of the x-ray source 140 over a range of vertical and horizontal positions. Height settings for the x-ray source 140 can range from low height for imaging feet and lower extremities to shoulder height and above for imaging the upper body portions of patients in various positions.

Figure 2:
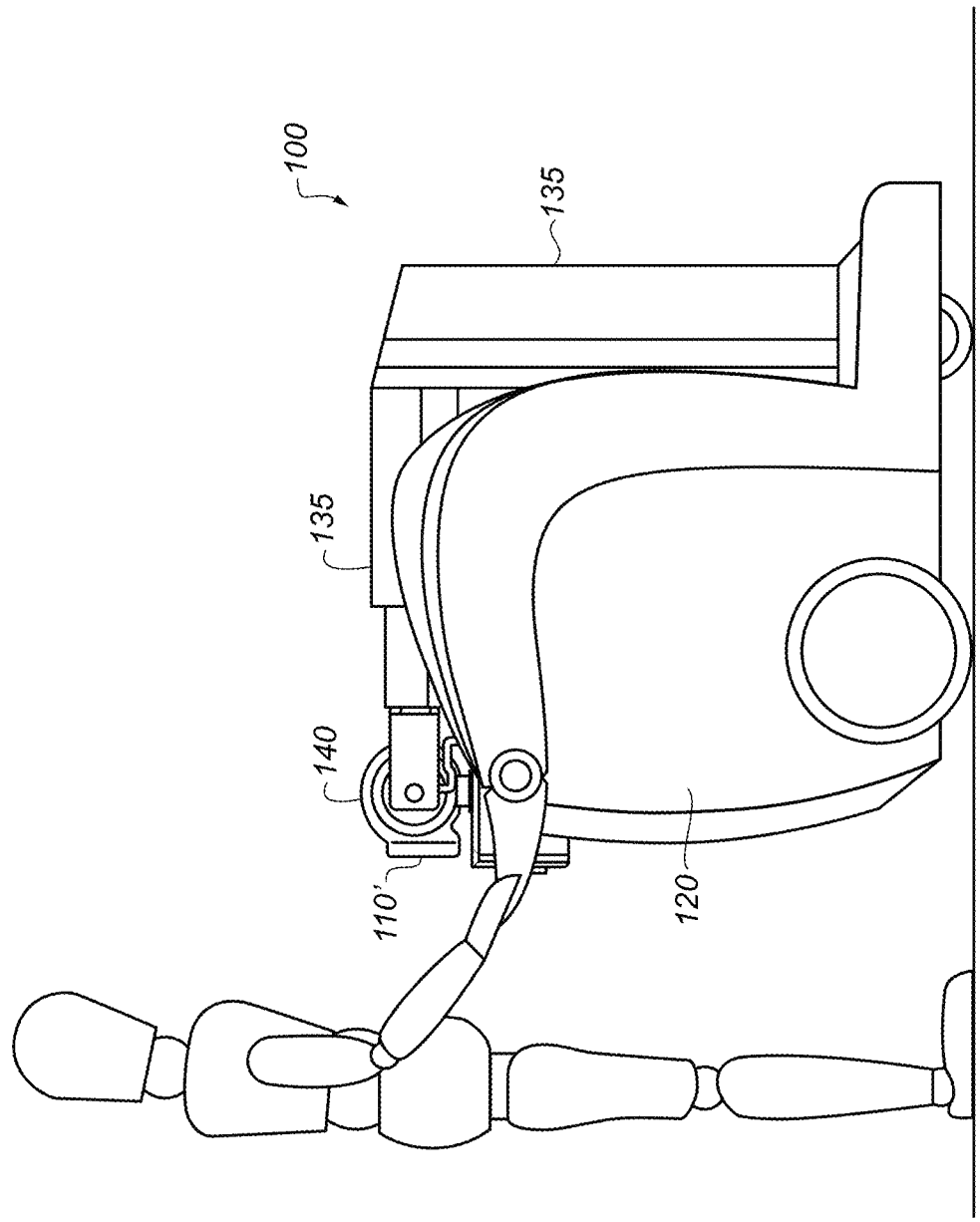
FIG. 2 is a diagram that shows a perspective view of a mobile radiography unit of FIG. 1 positioned for travel.

As shown in FIG. 2, for ease during transport of the mobile radiographic apparatus 100, the support member 135 and x-ray source 140 can be arranged close to frame 120. As shown in FIG. 2, the second display 110' can be in a viewable position (e.g., operable) during transport of the mobile radiographic apparatus 100. When the mobile radiographic apparatus 100 is to be used, the support member 135 and x-ray source 140 can be extended from the frame 120 for proper positioning (e.g., by the operator, a user, or x-ray technician) and the second display 110' moved to viewable position such as shown in FIG. 1.

Figure 3:
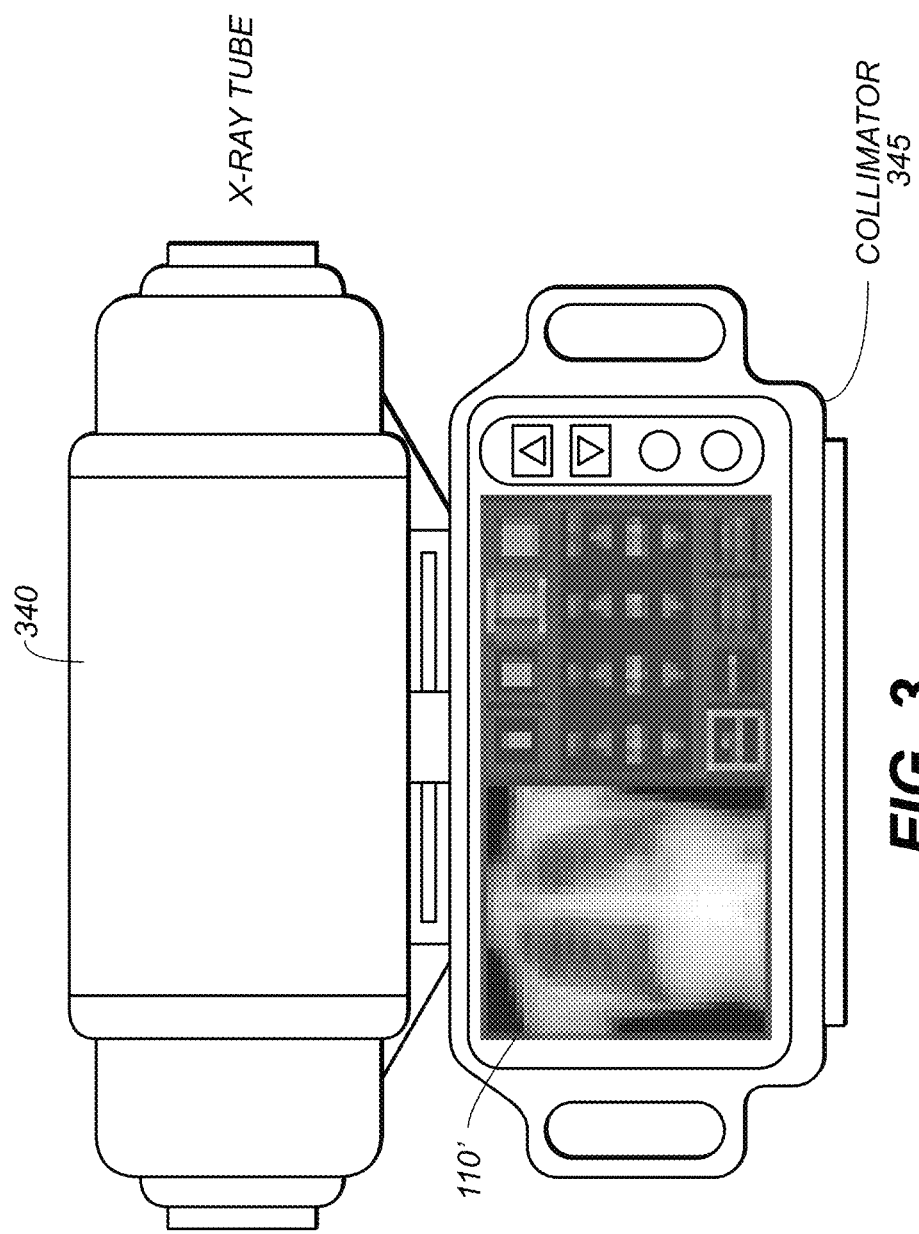
FIG. 3 is a diagram that shows an exemplary embodiment of a display/monitor as a second display mounted to a boom assembly of a mobile radiography unit according to the application.

FIG. 3 is a diagram that shows an exemplary embodiment of a display/monitor as a second display mounted to a boom assembly of a mobile radiography unit according to the application. As shown in FIG. 3, the second display 110' can be mounted to a collimator 345 of an x-ray source 340 of a support member 135 of a mobile radiography unit. In one embodiment, the collimator 345 can be rotatably mounted to the x-ray source 340 so that the collimator 345 (e.g., second display 110') can swivel at least 90 degrees, at least 180 degrees or 360 degrees plus. As shown in FIG. 3, the second display 110' is coupled to a plurality of handles for ease of positioning. Alternatively, the second display 110' can be mounted to (e.g., rotatably) an x-ray source 340 above a collimator 345 of a boom assembly of a mobile radiography unit.

Figure 4:
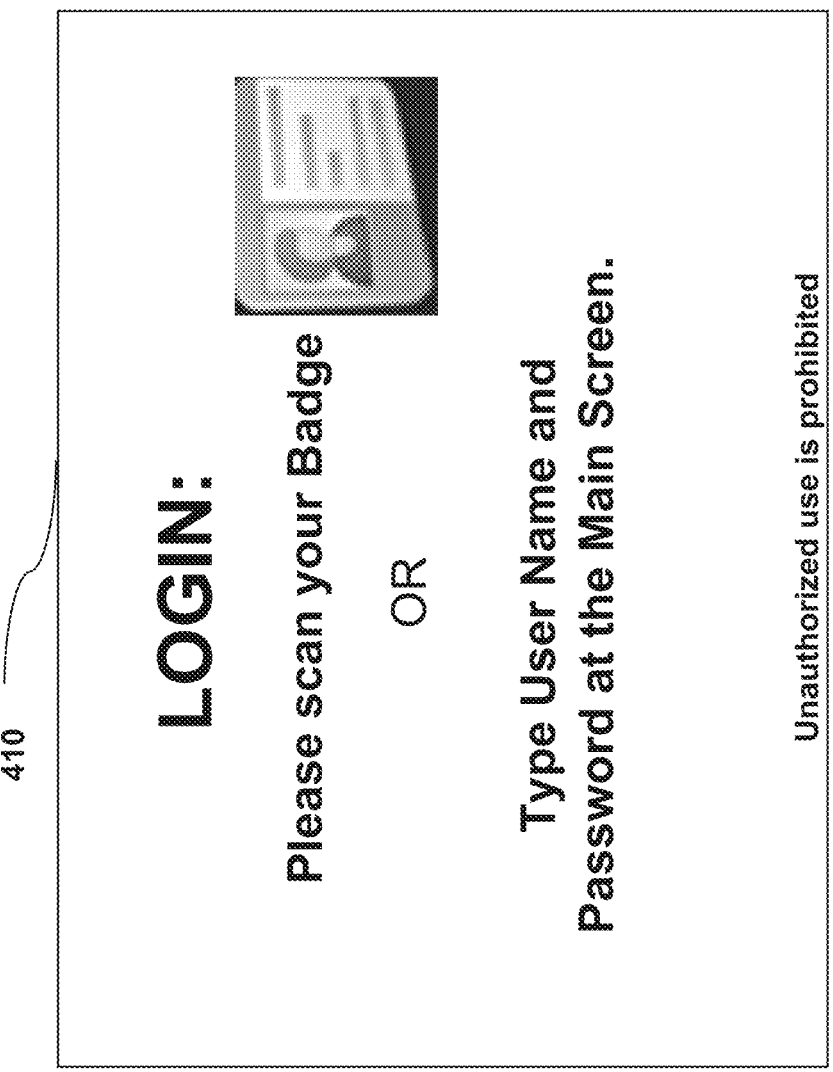
FIG. 4 is a diagram that illustrates an embodiment of a single sign on screen according to the application.

FIG. 4 is a diagram that illustrates an embodiment of a sign on screen according to the application. Thus, when an attempt is made to operate the mobile x-ray imaging apparatus 100, a sign on screen 410 can be displayed to provide instructions to a user. As shown in FIG. 4, the single sign on screen 410 can provide instructions for sign on sign on and activate the mobile x-ray system 100 such as "LOGIN: Please scan your badge or type User Name and Password at the main screen." Exemplary embodiments of a pass key or ID badge can include but are not intended to be limited to a card reader such as a smart card, a magnetic stripe card, bar code data, or a proximity reader compatible with access technologies such as RFID, bluetooth, wireless communication device, a proximity card, a wireless smart card, a wiegand card, a magnetic reader device/card, an optical reader device/card, an infrared reader device/card, or biometric data such as fingerprints, eye scan or the like.

According to exemplary embodiments of the application, the first display 110 and the second display 110' can provide information such as but not limited to: (i) general information such as date, time, environment conditions, and the like; (ii) unit information such as model serial number, operating instructions, warning information, and the like; (iii) patient data, such as patient name, room number, age, blood type, and the like; (iv) indicators such as but not limited to cart power/battery indicators, detector status (e.g., on/off), wireless signal strength/connectivity, grid alignment aides, cart diagnostics and/or (v) imaging/procedure information, such as the exam type, exposure information, and the like.

According to embodiments of the application, the first display 110 and the second display 110' can provide capabilities/functionality to the mobile x-ray imaging apparatus 100 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display and/or change a Patient Worklist, such as a list of exams to perform and allow the user to select an exam. (In one embodiment, such a patient worklist can be automatically updated (e.g., synchronized to a master/hospital/doctor worklist) using a wired or wireless network/connection. In one embodiment, the mobile x-ray imaging apparatus 100 can highlight/indicate new exams (e.g., on the second display 110') upon receipt of the scheduled examination.); (v) display generator/source current values and controls to change those values, such as: kVp, mA, mAs, Time. ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile x-ray imaging apparatus 100 during transport, e.g., using a video camera located on the other side (e.g., front side of the mobile x-ray imaging apparatus 100). In one embodiment, the mobile x-ray system 100 can include a collision avoidance system with alerts (e.g., audible, visual), and automatic maneuvering to avoid contact in the examining room (e.g., by stopping or course modification).

Figure 6:
Figure 7:
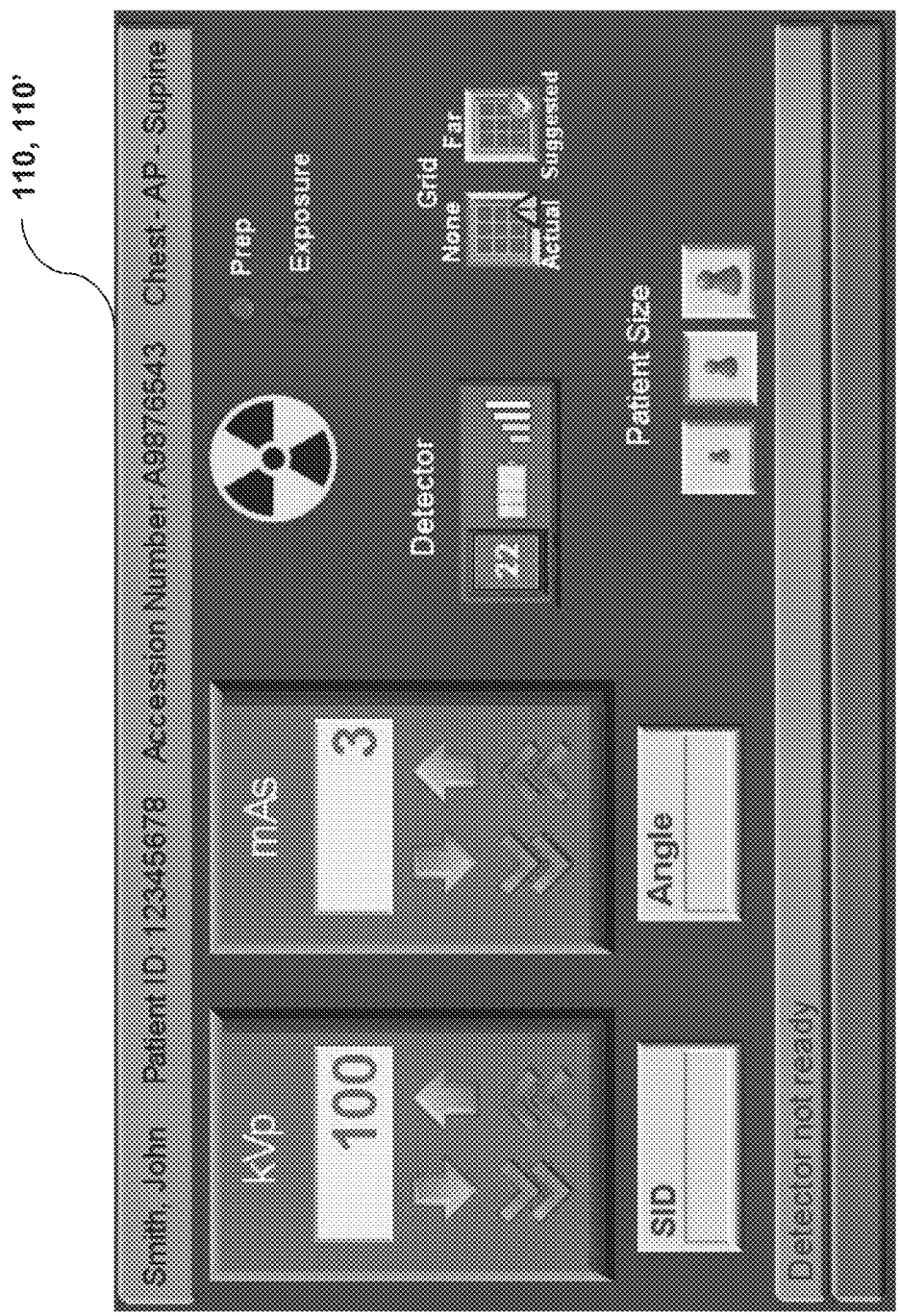
Figure 8:
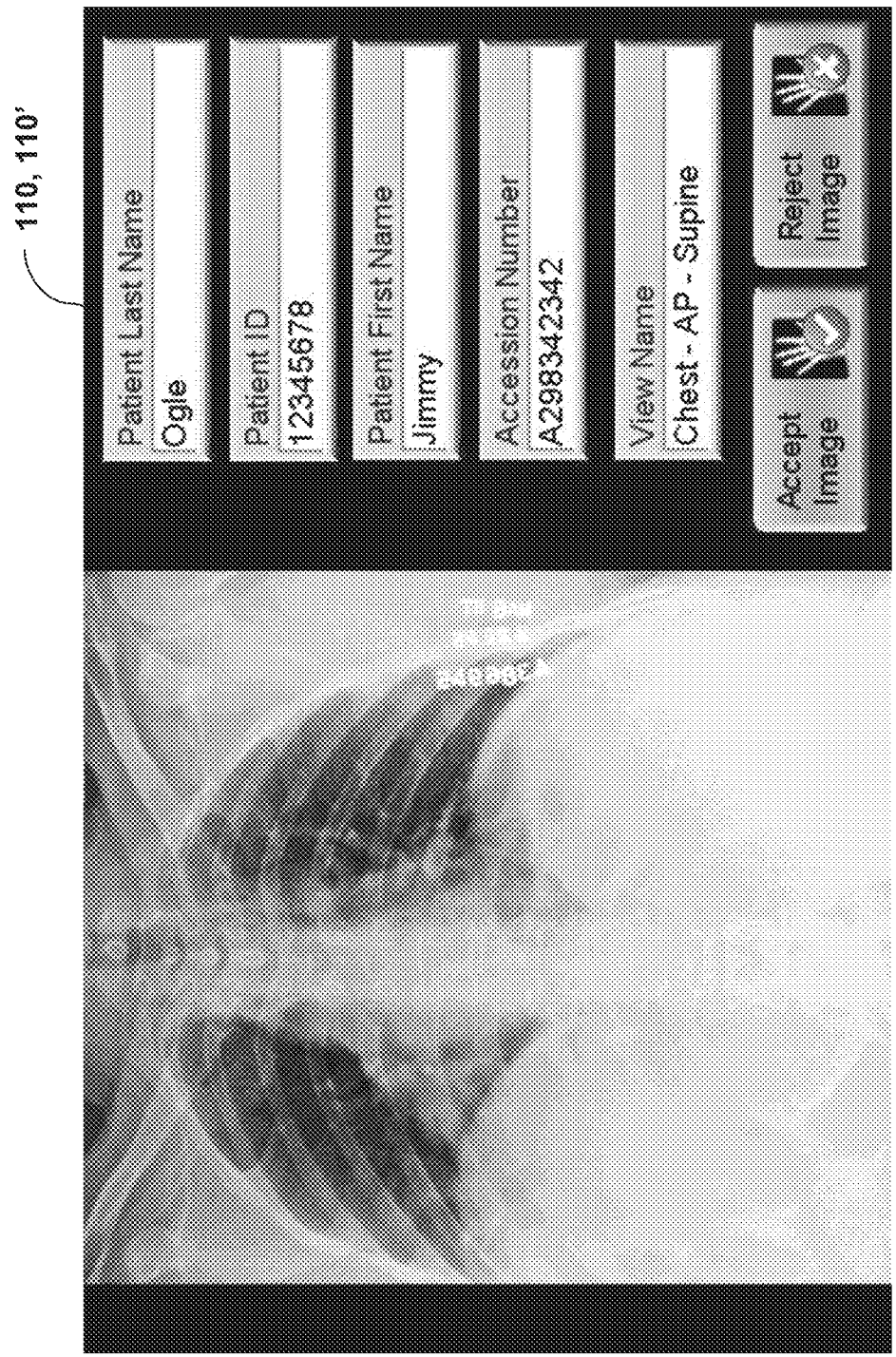

FIGS. 5-8 are diagrams that illustrate exemplary non-limiting representative functions illustrated on an embodiment of a first display and/or a second display of a mobile x-ray imaging apparatus. As shown in FIG. 5, an example of a work list is shown on a monitor of the second display 110'. As shown in FIG. 6, an example of a new examination/procedure information/requirement for that technician and/or patient is shown on a monitor of the second display 110'. As shown in FIG. 7, an example of x-ray source controls is shown on a monitor of the second display 110'. As shown in FIG. 8, an example of newly acquired image and patient information is shown on a monitor of the second display 110'.

In one embodiment, the mobile radiographic imaging apparatus can be operated/controlled by programmed control logic in the first or second displays. For example, the programmed control logic can include a processor and display, an integrated computer system, or a portable computer and applications to operate thereon.

Figure 9:
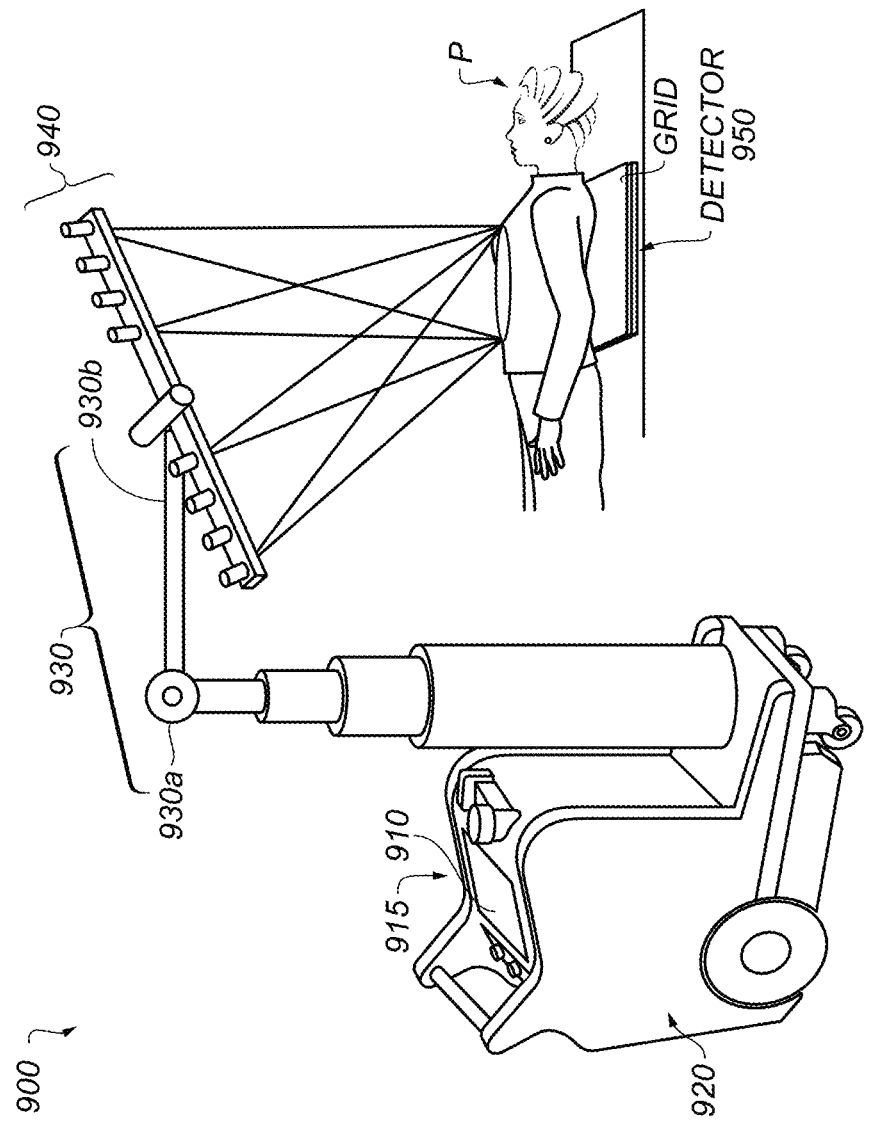
FIG. 9 is a diagram that shows a perspective view of a mobile radiography unit that can provide a tomosynthesis capability according to embodiments of the application.

FIG. 9 is a diagram that shows a perspective view of a mobile radiography unit that can provide a tomosynthesis capability according to embodiments of the application. In one embodiment, a mobile radiography unit that can further operate as a tomosynthesis system. As shown in FIG. 9, an embodiment of a mobile radiographic/tomosynthesis system 900 is shown that can include a movable transport frame 920. Mounted to the moveable transport frame 920 can be a support column that supports an x-ray source assembly 940. As shown in FIG. 9, a support column 930 can include a second section 930*b* that extends outward a fixed/variable distance from a first section 930*a*, where the second section 930*b* is configured to move (e.g., ride vertically) up and down the first section 930*a* to the desired height for obtaining the projection images. The system also includes a digital x-ray detector 950 that is wirelessly (e.g., or wired, tethered) connected to a system controller 915 contained inside the moveable transport frame 920. The system controller 915 can implement and/or control the functionality of the mobile radiographic/tomosynthesis system 900 (e.g., functionality provided through a console or control displays 100, 100'). The system controller 915 can be provided though one or more of a conventional general purpose processor, digital computer, microprocessor, RISC processor, signal processor, CPU, arithmetic logic unit (ALU), video digital signal processor (VDSP) and/or similar computational machines, programmed according to the teachings of the application, as will be apparent to those skilled in the relevant art(s).

In certain exemplary embodiments of mobile radiography units that can provide a tomosynthesis capability, a moveable mounted x-ray source can, in addition, be supplied with a plurality of multiple individually controlled x-rays sources (e.g., a distributed x-ray source array). FIG. 9 shows an embodiment of a mobile tomosynthesis system where multiple individually controlled x-rays sources comprise distributed x-ray sources (e.g., linearly distributed). As shown in FIG. 9, an x-ray source assembly can include a plurality of distributed x-ray power sources where at least one central source of the distributed x-ray power sources has full (e.g., standard) x-ray power. The central source can have a wide range of kVp settings, such as from 50 kVp to 150 kVp. and high maximum mA output, such as from 10 mA to 400 mA, in order to accommodate many different exam types for general radiography. The distributed sources can be arrayed in a prescribed spatial relationship. The distributed sources can be a lower power x-ray sources, which means a narrow range of kVp settings, such as from 60 kVp to 120 kVp. and lower maximum mA output, such as from 1 mA to 100 mA. Thus, as shown in FIG. 9, a mobile radiographic/tomosynthesis system 900 can include one or more, and preferably all of the capabilities of the mobile radiographic system 100 shown in FIG. 1. The x-ray source assembly 940 can use collimator(s) to form beams that are directed towards the detector 950 and/or patient P. The x-ray source assembly 940 may also include positioning, such as motors, which allow for directing the beam towards the detector 950 and/or patient P. The moveable transport frame 920 can include a first display 910, which can control at least the x-ray source assembly 940. Further, the system controller 915 can coordinate operations of the x-ray source assembly 940, detector 950, and moveable transport frame 920 (e.g., via operator actions using the first display 910). The system controller 915 can control operations of the x-ray source assembly, which may include the collimator, positioning devices and triggering of image acquisition by emission of x-rays from the sources. For example, the system controller 915 can control x-ray emission for CT imaging procedures and/or for general radiography imaging procedures. The system controller 915 also can control operations of the detector 950, which may include triggering of the image acquisition and transmission of the acquired images back to the controller. In addition, the system controller 915 can control the movement of the transport frame 920.

FIG. 10 is a diagram that shows exemplary mobile radiographic imaging systems including an x-ray source assembly that can include first and second (e.g., multiple) radiographic x-ray sources. As shown in FIG. 10, an x-ray source assembly 1040 of a mobile radiographic imaging system can include a first radiographic x-ray source and collimator, and a second x-ray source comprising a distributed sources (e.g., rectangle) that can be individually adjusted (e.g., collimated) and either permanently attached or attached (e.g., detachable) when needed. As shown in FIG. 10, in one embodiment, the first radiographic x-ray source can be a central one of the distributed sources. Alternatively, the first radiographic x-ray source is positioned at a center of the second array of distributed sources. As shown in FIG. 10, the first radiographic x-ray source can be a mobile/portable x-ray source/tube and be a different type of x-ray source from the second distributed array of lower power carbon-nanotube x-ray sources.

Figure 11:
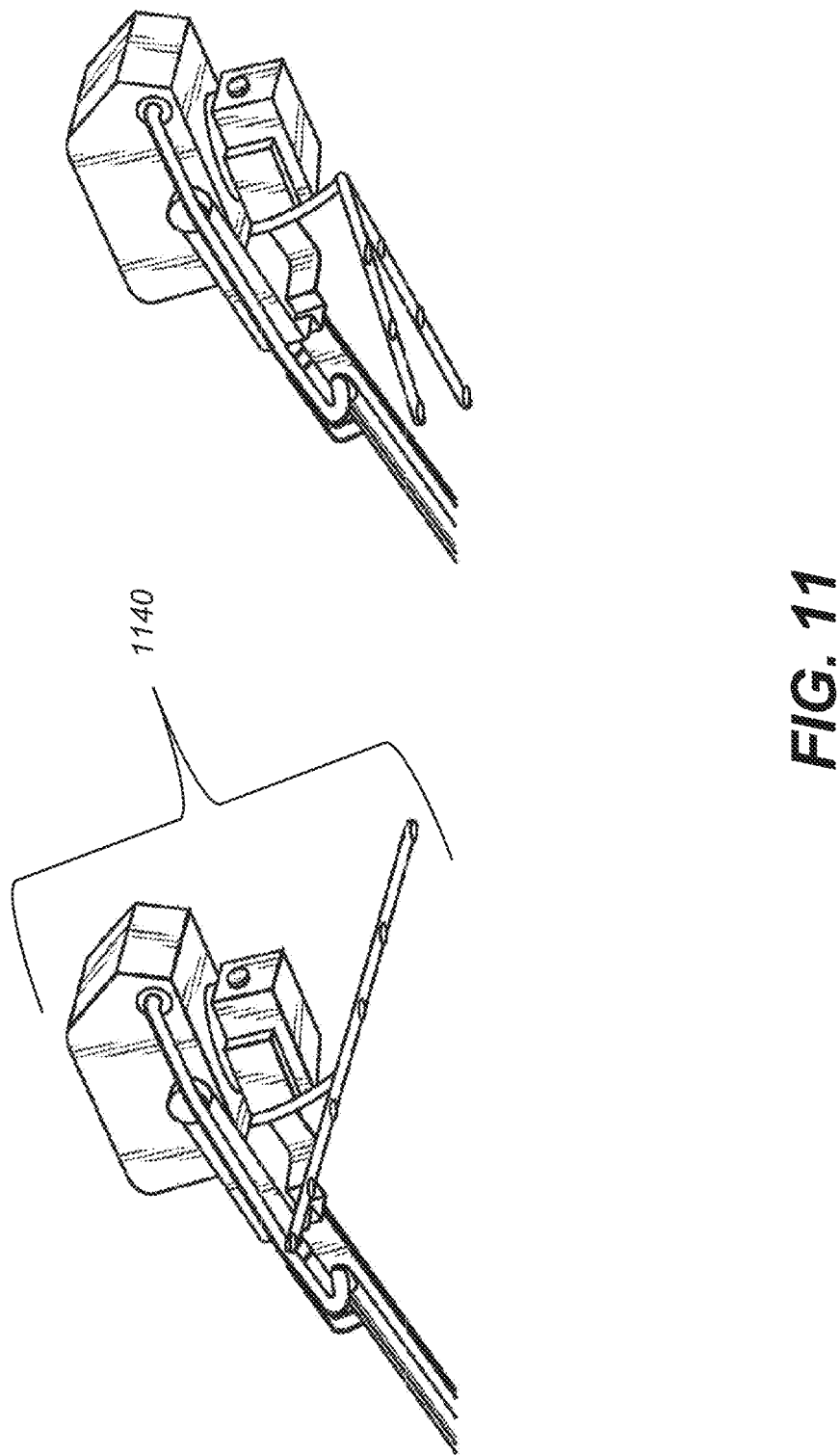
FIG. 11 is a diagram that shows exemplary mobile radiographic imaging systems including an x-ray source assembly embodiment that can include first and second radiographic x-ray sources according to the application.

FIG. 11 is a diagram that shows exemplary mobile radiographic imaging systems including an x-ray source assembly that can include first and second (e.g., multiple) radiographic x-ray sources. In one embodiment an x-ray source assembly 1140 of a mobile radiographic imaging system can include a directed first radiographic x-ray source and a directed second x-ray source comprising a distributed source attachment (e.g., linear) that can be either permanently attached or attached (detachable) when needed. As shown in FIG. 11, the first radiographic x-ray source can be positioned at a center of the array of distributed sources. In one embodiment, the first radiographic x-ray source can be a central one of the distributed sources. In one embodiment, the plurality of distributed x-ray sources can be mounted along a support. In one embodiment, the plurality of distributed x-ray sources can have a prescribed spatial relationship, where the prescribed spatial relationship is one or more linear tracks, 2D tracks, curves, polygons, rectangles or 3D paths. In one embodiment, collimated distributed sources can be on a curved support to maintain a single distance from a corresponding point on a detector. Exemplary distributed source attachment can have a first position for use and a second position for storage (e.g., folded) when not used.

Figure 12:
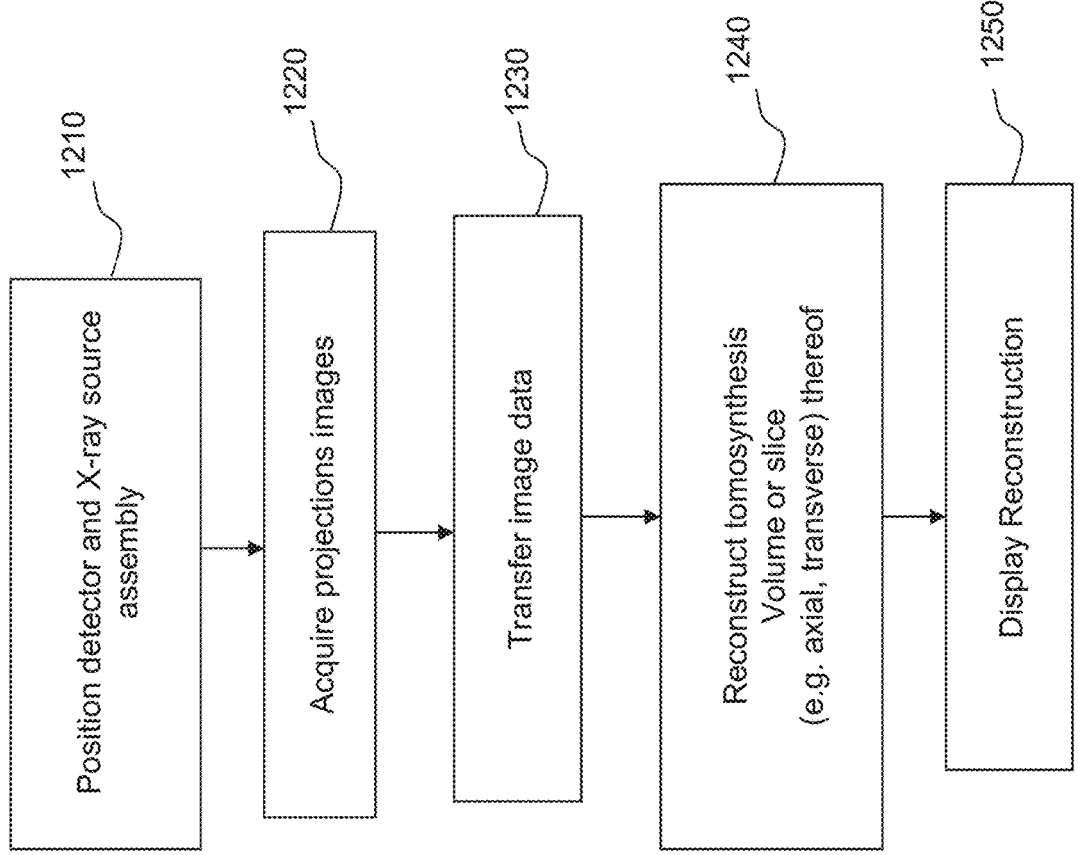
FIG. 12 is a flow chart that shows an exemplary method of operating exemplary mobile radiographic imaging systems for acquiring projections images and generating the reconstruction of three-dimensional tomosynthesis images.

Referring to FIG. 12, a flow chart that shows an exemplary method of acquiring projections images and generating the reconstruction of three-dimensional tomosynthesis images, will now be described. The method for acquiring projections images and generating the reconstruction of three-dimensional tomosynthesis images will be described using embodiments of mobile radiography apparatus shown in FIGS. 9-12 and can be applied to mobile x-ray systems/carts shown in FIGS. 1 and 9-12; however, the method of FIG. 12 is not intended to be limited thereby.

As shown in FIG. 12, the detector and x-ray source assembly can be positioned (operation block 1210). For example, the x-ray source can be moved to its initial position and the detector can be positioned such that the patient P is interposed between the detector and x-ray source.

For exemplary mobile radiographic/tomosynthesis system embodiments 900, the initial x-ray source assembly position can be set by the location of the transport frame and the support column. The height, extent and rotation positioning of the support column's first section 930a and the second section 930 can be used to position the x-ray source assembly to the initial desired location above the patient.

Then, a series of projections image can be acquired at different x-ray source positions (operation block 1220). In embodiment 900, the projection images can be acquired while individual x-ray sources are triggered. In one embodiment, the first radiographic x-ray source can operate as a central one of the distributed sources. In one embodiment, the first radiographic x-ray source can be a central one of the distributed sources.

Then, the acquired projection image data can be received (e.g., transferred back from the detector to the system) by control and processing components of the system controller (operation block 1230). The projection images can be displayed on display 110 and/or undergo a quality check (e.g., automated or by the operator) before being further processed. The projection image data may also be processed at operation block 1230 to permit raw, partially-processed or fully-processed images or tomosynthesis slices to be stored (e.g., temporality at the detector) and/or sent to remote locations.

Then, tomosynthesis image reconstruction can be performed (e.g., real-time) using the acquired corrected projection image data (operation block 1240). Image reconstruction can use processes similar to those used for conventional tomosynthesis imaging. For example, as will be appreciated by those skilled in the art, backprojection, filtered backprojection or other known reconstruction techniques may be used. In one exemplary embodiments, a particular position of the source with respect to the detector can be determined by knowledge of the position of the x-ray source assembly and the detector based upon the values set by an operator, automatically determined such as by using a grid alignment system to adjust the values or by a tethered connection therebetween.

Then, the reconstruction volume can be displayed on display 110, 110' (operation block 1250) and/or undergo a quality check before displaying the volume. In one embodiment, the reconstruction volume can be stored after the quality check (e.g., before display thereof). Further, the display can be used to view underlying projection images or projection images generated by the system, or the tomosynthesis reconstructions themselves. Further, underlying data and/or reconstructed tomosynthesis images can be transmitted to a remote system.

Exemplary mobile radiographic systems can include a portable x-ray generator/cart/tube/source machine and a wireless digital detector. The portable tomosynthesis capability/system can be configured by adding a distributed x-ray source array (e.g., to a mobile radiographic cart). The mobile tomosynthesis capability/system is configured to capture a series of relatively lower x-ray exposures of a patient's anatomy over a wide angle in rapid succession. In operation, the distributed x-ray source array can allow a sequence of images to be captured in rapid succession without requiring the x-ray source/assembly to move. Once the image sequence is captured, the images can be reconstructed into slice data of the anatomy, which can then be interpreted by a radiologist or ICU physician, at the site or remotely. Thus, certain exemplary embodiments herein can provide a single imaging system including a first mode of operations for general radiography projection imaging of an object (e.g., using the capabilities described with respect to at least FIG. 1) and a second mode of operations for x-ray tomosynthesis imaging of an object (e.g., using the capabilities described with respect to at least FIG. 9).

In certain exemplary embodiments, a mobile radiographic imaging system including a tomosynthesis capability can support critically ill patients in an ICU that are currently transported out of ICU for x-ray imaging. For example, ICU patients can receive a tomosysthesis procedure in the ICU that might otherwise be transported out of ICU in order to obtain a CT exam. For example, CT imaging is often needed for ICU patients in order to differentiate various types of fluids induced by plural effusions, such as blood, water, and the like, so that corrective actions can be taken. However, transporting ICU patients to the CT exam area can be a challenging task because of their severe clinical conditions. Further, visualization software can be provided to facilitate interpretation of ICU-related chest abnormalities. For instance, presentation of the low exposure sequences (prior to reconstruction of the slide data) can allows the ICU physician (local or remote) to "look around" rib structures and the like.

For such reasons. Applicants have recognized that it is highly desirable to have a three-dimensional imaging modality at the bedside directly in the ICU department so a patient does not have to be moved unnecessarily. Applicants have devised a portable bedside tomosynthesis, by modifying exemplary digital mobile radiographic systems, for example, by adding a combined x-ray source assembly.

Tomosynthesis requires features such as precise measurements of the x-ray source/tube focal point position, x-ray pointing direction, detector position and orientation, and source-to-detector distance. These features needed for tomosynthesis, however, are a challenge for portable or mobile digital imaging systems where the detector does not have any mechanical link to the x-ray source/tube.

Applicants have further recognized that advancements in grid alignment development for mobile/portable radiographic imaging provide for precise alignment of the x-ray source/tube and the portable detector/grid. Accordingly, certain exemplary embodiments herein can provide a system configured to detect the x-ray source/tube position and orientation relative the detector within mm precision, which can be sufficient for the tomosynthesis application. Embodiments disclosed herein can be related to and/or incorporate capabilities in pending U.S. patent application Ser. No. 13/283,654, Alignment Apparatus for X-ray Imaging System, the disclosure of which is incorporated by reference in its entirety. Alternatively, suitable grid alignment methods can use RF triangulation, optical reference markers, ultrasound, and the like for position reporting.

Additional exemplary features of a mobile radiographic imaging system embodiments including a tomosynthesis capability can include: computer aided analysis of the slide data to differentiate among various pleural and airway abnormalities; automatic detection of tube and catheter tip placements and automatic notification to the ICU physician if a tube or catheter tip is misplaced; and/or a central X-ray source on the array that has full (standard) X-ray power such that the system can be used for capturing a standard exams (e.g., portable chest-ray). Certain exemplary embodiments herein can further provide a human interface device coupled to the console or system controller to allow display and/or manipulation to control such tomosynthesis capabilities.

Applicants have noted that such exemplary embodiments described herein are desirable in an intensive care unit (ICU), where chest x-rays are often acquired. Accordingly, in one embodiment, a mobile radiographic/tomosynthesis system can be focused on the chest.

Exemplary implementations of the embodiment shown in FIG. 9 can include spatial extent of spar or support for the distributed tomosynthesis x-ray sources, which can be lower power sources providing mAs per nanotube x-ray source, a number of sources, a wireless digital detector, a grid & alignment system, and a mobile cart/device with portable x-ray source/tube.

Various exemplary embodiments described herein can illustrate individual modes of operation. In certain exemplary embodiments, more than one mode can be provided in/by a single mobile radiographic imaging system and/or methods for using the same.

Consistent with at least one embodiment, exemplary systems/methods can use a computer program with stored instructions that perform on image data that is accessed from an electronic memory. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products of this application may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

Exemplary functions performed by the diagrams of FIG. 12, the system processor or the mobile radiographic unit may be implemented, for example, but not limited to using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU). GPU, video digital signal processor (VDSP) and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software is generally executed from a medium or several media by one or more of the processors of the machine implementation.

It should be noted that while the application description and examples are primarily directed to radiographic medical imaging of a human or other subject, embodiments of apparatus and methods of the application can also be applied to other radiographic imaging applications. This includes applications such as non-destructive testing (NDT), for which radiographic images may be obtained and provided with different processing treatments in order to accentuate different features of the imaged subject.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A mobile x-ray radiography system, comprising:
a moveable transport frame comprising wheels configured to move the transport frame over a surface to an intended location;
an adjustable support structure coupled to the moveable transport frame, the adjustable support structure configured to be rotatable with respect to the transport frame;
an x-ray source assembly mounted to the adjustable support structure, wherein the adjustable support structure allows movement of the x-ray source assembly over a range of independent vertical and horizontal positions, the x-ray source assembly configured to direct x-ray radiation toward a subject from a plurality of different sources, the X-ray source assembly including:
a first type x-ray source configured to emit x-ray radiation at a first power level from a first position toward the subject to generate a projection radiographic image of the subject, and
a plurality of second type distributed x-ray sources all disposed to one side of the first type x-ray source and each configured to emit x-ray radiation toward the subject at a second power level less than the first power level to generate multiple projection images used for reconstruction of tomosynthesis images, the first type x-ray source and the plurality of second type distributed x-ray sources fixed in a spatial relationship relative to each other, wherein the second type distributed x-ray sources are configured to emit x-ray radiation one at a time toward the subject;
processing circuitry at the mobile x-ray radiography system configured to receive any projection radiographic image of the subject and any multiple projection images of the subject used for reconstruction of tomosynthesis images, wherein the processing circuitry is configured to reconstruct a tomosynthesis image of the subject at the mobile radiography apparatus; and a portable power supply configured to provide power for the mobile x-ray radiography system.

2. The system of claim 1, further comprising a user interface device coupled to the processing circuitry, the user interface device configured to receive inputs from a user to initiate the capture of the multiple projection images used for the reconstruction of the tomosynthesis images.

3. The mobile x-ray radiography system of claim 1, wherein the plurality of second type distributed x-ray sources are fixed in a linear arrangement to one side of the first type x-ray source.

4. The mobile x-ray radiography system of claim 1, further comprising a digital radiographic detector disposed proximate a subject to capture the multiple projection images of the subject used for reconstruction of tomosynthesis images of the subject.

5. The mobile x-ray radiography system of claim 4, wherein the digital radiographic detector is configured to wirelessly transmit the captured multiple projection images of the subject to the processing circuitry.

6. The mobile x-ray radiography system of claim 4, wherein the digital radiographic detector comprises electronic memory to store the captured multiple projection images of the subject.

7. The mobile x-ray radiography system of claim 4, wherein the digital radiographic detector is tethered by wire to the mobile x-ray radiography system to transmit the captured multiple projection images of the subject to the processing circuitry.

8. The mobile x-ray radiography system of claim 4, wherein the x-ray source assembly and the digital radiographic detector are configured to each remain stationary while capturing the multiple projection images of the subject.

9. The mobile x-ray radiography system of claim 1, wherein the plurality of second type distributed x-ray sources each comprise a carbon nanotube.

10. The mobile x-ray radiography system of claim 9, wherein the first type x-ray source comprises a standard projection radiography x-ray source.

11. A mobile x-ray radiography system, comprising:
a wheeled transport frame;
an adjustable support structure coupled to the moveable transport frame;
an x-ray source assembly comprising a plurality of different x-ray sources, the x-ray source assembly mounted to the adjustable support structure, wherein the adjustable support structure is configured to allow movement of the x-ray source assembly over a range of independent vertical and horizontal positions, and wherein the plurality of different x-ray sources includes:
a first x-ray source configured to emit full power x-rays for projection radiography; and
a plurality of distributed x-ray sources disposed in a fixed spatial relationship proximate the first x-ray source, the plurality of distributed x-ray sources each configured to emit x-rays having a lower power than the first x-ray source to generate a projection image data set used for reconstruction of tomosynthesis images;

processing circuitry at the mobile x-ray radiography system configured to receive a projection radiographic image acquired by using the first x-ray source and to receive the projection image data set acquired by using the plurality of distributed x-ray sources; and a portable power supply configured to power the mobile x-ray radiography system, wherein the processing circuitry is configured to process the received projection radiographic image at the mobile radiography apparatus, and to reconstruct a tomosynthesis image from the received projection image data set at the mobile radiography apparatus.

12. The system of claim 11, further comprising a user interface configured to receive inputs from a user to initiate acquisition of the projection radiographic image and the projection image data set.

13. The mobile x-ray radiography system of claim 11, wherein the distributed x-ray sources are fixed in a V formation to one side of the first x-ray source.

14. The mobile x-ray radiography system of claim 1, further comprising a digital radiographic detector disposed proximate a subject to capture the projection radiographic image of the subject and the projection image data set of the subject.

15. The mobile x-ray radiography system of claim 14, wherein the digital radiographic detector is configured to wirelessly transmit the captured projection radiographic image of the subject and the projection image data set of the subject.

16. The mobile x-ray radiography system of claim 14, wherein the digital radiographic detector comprises electronic memory to store the captured projection radiographic image of the subject and the projection image data set of the subject.

17. The mobile x-ray radiography system of claim 14, wherein the digital radiographic detector is tethered by wire to the mobile x-ray radiography system to transmit the captured projection radiographic image of the subject and the projection image data set of the subject.

18. The mobile x-ray radiography system of claim 14, wherein the x-ray source assembly and the digital radiographic detector are configured to each remain stationary while capturing the projection radiographic image of the subject and the projection image data set of the subject.

19. The mobile x-ray radiography system of claim 11, wherein the plurality of distributed x-ray sources each comprise a carbon nanotube.

20. The mobile x-ray radiography system of claim 19, wherein the processing circuitry is configured to wirelessly transmit the received and processed projection radiographic image, the reconstructed tomosynthesis image, or both.

* * * * *

UNITED STATES PATENT AND TRADEMARK OFFICE
CERTIFICATE OF CORRECTION

PATENT NO. : 10,463,325 B2  
APPLICATION NO. : 16/003653  
DATED : November 5, 2019  
INVENTOR(S) : David H. Foos et al.

Page 1 of 1

It is certified that error appears in the above-identified patent and that said Letters Patent is hereby corrected as shown below:

On the Title Page

Item (60),  
Related U.S. Application Data,  
Page 2

Please replace "Provisional application No. 62/601,663, filed on Feb. 22, 2012." with --Provisional application No. 61/601,663, filed on Feb. 22, 2012.--

Signed and Sealed this  
Twenty-fourth Day of December, 2019

Andrei Iancu  
*Director of the United States Patent and Trademark Office*